United States Patent
Martin et al.

(10) Patent No.: US 6,524,865 B1
(45) Date of Patent: *Feb. 25, 2003

(54) ELECTROCHEMILUMINESCENT ENZYME IMMUNOASSAY

(75) Inventors: Mark T. Martin, Bethesda; Rick Saul, Gaithersburg, both of MD (US); Pam Liang, Arlington, VA (US)

(73) Assignee: IGEN International, Inc., Gaithersburg, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/928,075

(22) Filed: Sep. 11, 1997

Related U.S. Application Data

(63) Continuation of application No. 08/484,766, filed on Jun. 7, 1995, now abandoned.

(51) Int. Cl.$^7$ ...................... G01N 21/76; G01N 33/563; G01N 33/53; C12Q 1/34
(52) U.S. Cl. ...................... 436/172; 436/501; 436/512; 436/513; 435/7.6; 435/7.72; 435/18; 435/7.9; 435/7.95
(58) Field of Search ............................... 435/7.1, 7.72, 435/7.9, 7.01, 7.92, 18, 23, 24, 25, 966, 968, 975, 7.6, 7.95; 436/172, 501, 512, 513; 252/700

(56) References Cited

U.S. PATENT DOCUMENTS

| | | | |
|---|---|---|---|
| 4,470,459 A | | 9/1984 | Copland |
| 4,818,709 A | * | 4/1989 | Primus et al. |
| 4,978,613 A | * | 12/1990 | Bieniaz et al. ................ 435/18 |
| 5,061,445 A | | 10/1991 | Zoski et al. |
| 5,068,808 A | | 11/1991 | Wake |
| 5,147,806 A | | 9/1992 | Kamin et al. |
| 5,221,605 A | | 6/1993 | Bard et al. |
| 5,238,808 A | | 8/1993 | Bard et al. |
| 5,247,243 A | | 9/1993 | Hall et al. |
| 5,264,346 A | | 11/1993 | Chen |
| 5,296,191 A | | 3/1994 | Hall et al. |
| 5,310,687 A | | 5/1994 | Bard et al. |
| 5,641,623 A | * | 6/1997 | Martin ........................... 435/4 |

FOREIGN PATENT DOCUMENTS

WO    WO 84/03303    8/1984

OTHER PUBLICATIONS

Chapter 11: "Inflammation" Section B: Enzyme–Linked Immunoabsorbent Assay in Basic & Clinical Immunology, 8th Edition, 1994: Appleton & Lange at p. 173–174 and see Figures therein.*

Promega Catalog, p. 14.27.*
Enzyme Nomenclature. Internation Union of biochemist and Molecular Biologist. Academic Press, New York, New York, pp. v–xiii, 1992.*
Yang et al., "Electrochemiluminescence: A New Diagnostic and Research Tool", 12 Bio/Technology 193–194 (2/94).
Blackburn et al., "Electrochemiluminescence Detection for Development of Immunoassays and DNA Probe . . . ", vol. 27, No. 9 Clin. Chem., 1534–1539 (1991).
D.J. Payne, "Metallo–B–lactamases—a new therapeutic challenge", 39 J. Med. Microbiol. 93–99 (1993).
S. Coulton and I. Francois, "6 B–Lactamases: Targets for Drug Design", 31 Progress in Medicinal Chemistry, 297–349 (1994).
Harold C. Neu, "The Crisis in Antibiotic Resistance", 257 Science, 1064–1072 (Aug. 21, 1992).
A.C. Peterson et al., "Evaluation of four qualitative methods for detection of B–lactamases . . . " vol. 8, No. 11 cur. J. Clin. Microbiol. Infect. Dis., 962–967 (1989) (not currently available).
Yolken et al., "Rapid diagnosis of infections caused by B–lactamase–producing bacteria . . . " vol. 97, No. 5 The Journal of Pediatrics, 715–720 (11/80).
S.C. Anderson and S. Cocayne, Clinical Chemistry: Concepts and Applications, W.B. Saunders (1993) Philadelphia, PA (currently not available).
Yolken et al., "The Uses of Beta–Lacatamase in Enzyme Immunoassays for Detection . . . " 73 J. Immunol. Meth., 109–123 (1984).
Svensson et al., "Synthesis and Characterization of Monoclonal Antibody–B–Lactamases Conjugates" 5 Bioconjugate Chem., 262–267 (1994).

* cited by examiner

Primary Examiner—Jyothsna Venkat
Assistant Examiner—Tomas Friend
(74) Attorney, Agent, or Firm—Kramer Levin Naftalis & Frankel LLP; Barry Evans, Esq.

(57) ABSTRACT

Electrochemiluminescent-labels and enzyme substrates, which preferably are conjugated, are used in immunoassays and electrochemiluminescence is generated catalytically. In conventional electrochemiluminescence immunoassays, an anti-analyte antibody molecule can give rise to typically 6–8 electrochemiluminescence-active ruthenium atoms, while in the present invention, each enzyme-labeled anti-analyte molecule can give rise to thousands of electrochemiluminescence-active ruthenium atoms per second. An exemplary immunoassay is based on a catalytic process employing β-lactamase-conjugated anti-analytes which enzymatically hydrolyze electrochemiluminescent-labeled substrates, making them strongly electrochemiluminescent. The electrochemiluminescence signal generated by each anti-analyte molecule (i.e., each analyte molecule) is much greater than with the conventional method. Accordingly, greater sensitivity can be gained in the measurement of low concentrations of a given immunoassay analyte.

13 Claims, 14 Drawing Sheets

AMPICILLIN

AMOXICILLIN

CEFOXITIN

PENICILLIN G

MOXALACTAM

ELECTROCHEMILUMINESCENT ENZYME IMMUNOASSAY

This application is a continuation of application Ser. No. 08/484,766, filed Jun. 7, 1995 now abandoned.

BACKGROUND OF THE INVENTION

1. Field of the Invention

The present invention relates to the development of an electrochemiluminescence (ECL) based enzyme immunoassay for the detection and the quantitative measurement of analytes. The immunoassay is based on a catalytic process employing β-lactamase-conjugated anti-analytes which enzymatically hydrolyze electrochemiluminescent substituted substrates, making them strongly electrochemiluminescent. The immunoassay is very sensitive and is suitable for the detection and monitoring of any analyte for which an anti-analyte can be made.

2. Description of Related Art

An ever-expanding field of applications exists for rapid, highly specific, sensitive, and accurate methods of detecting and quantifying chemical, biochemical, and biological substances, including enzymes such as may be found in biological samples. Because the amount of a particular analyte of interest such as an enzyme in a typical biological sample is often quite small, analytical biochemists are engaged in ongoing efforts to improve assay performance characteristics such as sensitivity.

One approach to improving assay sensitivity has involved amplifying the signal produced by a detectable label associated with the analyte of interest. In this regard, luminescent labels are of interest. Such labels are known which can be made to luminesce through photoluminescent, chemiluminescent, or electrochemiluminescent techniques. "Photoluminescence" is the process whereby a material luminesces subsequent to the absorption by that material of light (alternatively termed electromagnetic radiation or emr). Fluorescence and phosphorescence are two different types of photoluminescence. "Chemiluminescent" processes entail the creation of the luminescent species by a chemical reaction. "Electrochemiluminescence" is the process whereby a species luminesces upon the exposure of that species to electrochemical energy in an appropriate surrounding chemical environment.

The signal in each of these three luminescent techniques is capable of very effective amplification (i.e., high gain) through the use of known instruments (e.g., a photomultiplier tube or pmt) which can respond on an individual photon by photon basis. However, the manner in which the luminescent species is generated differs greatly among and between photoluminescent, chemiluminescent, and electrochemiluminescent processes. Moreover, these mechanistic differences account for the substantial advantages as a bioanalytical tool that electrochemiluminescence enjoys vis a vis photoluminescence and chemiluminescence. Some of the advantages possible with electrochemiluminescence include: (1) simpler, less expensive instrumentation; (2) stable, nonhazardous labels; and (3) increased assay performance characteristics such as lower detection limits, higher signal to noise ratios, and lower background levels.

As stated above, in the context of bioanalytical chemistry measurement techniques, electrochemiluminescence enjoys significant advantages over both photoluminescence and chemiluminescence. Moreover, certain applications of ECL have been developed and reported in the literature. U.S. Pat. Nos. 5,147,806, 5,068,808, 5,061,445, 5,296,191, 5,247, 243, 5,221,605, 5,238,808 and 5,310,687, the disclosures of which are incorporated herein by reference, detail certain methods, apparatuses, chemical moieties, inventions, and associated advantages of ECL.

A particularly useful ECL system is described in a paper by Yang et al., *Bio/Technology*, 12, pp. 193–194 (Feb. 1994). See also a paper by Massey, *Biomedical Products*, October 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al. (1991) *Clin. Chem.* 37/9, pp. 1534–1539, the authors used the ECL reaction of ruthenium (II) tris (bipyridyl), $Ru(bpy)_3^{2+}$ are very stable, water-soluble compounds that can be chemically modified with reactive groups on one of the bipyridyl ligands to form activated species with which proteins, haptens, and nucleic acids are readily labeled.

Beta-lactamases which hydrolyze the amide bonds of the β-lactam ring of sensitive penicillins and cephalosporins are widely distributed amongst microorganisms and play a role in microbial resistance to β-lactam antibiotics. Beta-lactamases constitute a group of related enzymes which are elaborated by a large number of bacterial species but not by mammalian tissues and can vary in substrate specificities. See generally Payne, D. J., *J. Med. Micro* (1993) 39, pp. 93–99; Coulton, S. & Francois, 1., *Prog. Med. Chem.* (1994) 31, 297–349; Moellering, R. C., Jr., *J. Antimicrob. Chemother.* (1993) 31 (Suppl. A), pp. 1–8; and Neu, H. C., *Science* (1992) 257, pp. 1064–1072.

Several methods currently exist for the detection of microbial β-lactamases. Some representative examples follow.

W. L. Baker, "Co-existence of β-lactamase and penicillin acylase in bacteria; detection and quantitative determination of enzyme activities", *J. Appl. Bacteriol.* (1992) Vol. 73, No. 1, pp. 14–22 discloses a copper-reducing assay for the detection of penicilloates and fluorescamine assay to detect 6-aminopenicillanic acid concentrations when both substances were produced by the action of the enzymes on a single substrate.

U.S. Pat. No. 5,264,346 discloses a calorimetric assay for β-lactamase which has a variety of applications. The assay is based on the decolorization of a chromophore formed by oxidation of either the N-alkyl derivative of p-phenylenediamine or the 3,3',5,5'-tetraalkyl derivative of benzidine. The decolorization is attributed to the presence of an open β-lactam ring product resulting from the hydrolysis of cephalosporin or penicillin. Decolorization with the open β-lactam product of penicillin requires the presence of a decolorization enhancer such as mercury containing compounds. The enhancer is not required for decolorization with the open β-lactam product of cephalosporin.

U.S. Pat. No. 4,470,459 discloses a rapid method for the detection of the presence of β-lactamase from microbial sources which is based on a β-lactamase conversion of a β-lactam substrate which reverses its ability to fluoresce. Specific β-lactams mentioned as having this property include ampicillin, cephalexin, amoxicillin, cefadroxil and cephaloglycin. The change in the ability to fluoresce is attributed to the presence of β-lactamase.

WO 84/03303 discloses a microbiological test process for identifying producers of β-lactamase. The assay relies on changes in acidity which affect the fluorescence of the indicator such as coumarin. This change in acidity is attributed to the conversion product produced by the presence of the β-lactamase.

A. C. Peterson et al., "Evaluation of four qualitative methods for detection of β-lactamase production in Staphylococcus and Micrococcus species", *Eur. J. Clin. Microbiol. Infect. Dis.* (1989), Vol. 8, No. 11, pp. 962–7 presents certain factors which were employed in evaluating qualitative assays for β-lactamase.

Robert H. Yolken et al., "Rapid diagnosis of infections caused by β-lactamase-producing bacteria by means of an enzyme radioisotopic assay", *The Journal of Pediatrics*, Vol. 97, No. 5 (November 1980) pp. 715–720 discloses a sensitive enzymatic radioisotopic assay for the measurement of β-lactamase as a rapid test for detection of bacterial infection. The assay protocol involves an incubation step with sample followed by the separation step on a positively charged column such as DEAE-Sephacel prior to measurement of the radioactivity of eluted fractions. The β-lactamase converted penicillinic product has an additional carboxyl group which insures its stronger binding to the positively charged column than the penicillin. Differences in radioactivity between the eluted fractions and the original values are attributed to the presence of β-lactamase.

In immunoassays generally, antibodies (equivalently referred to herein as "anti-analytes") are used to detect analyte. Commonly, an anti-analyte is labeled with a molecule that is detectable by, for example, absorbance, fluorescence, luminescence, or electrochemiluminescence. Alternatively, the antibody can be labeled with an enzyme that creates or destroys a compound with one of these features. There are two main types of enzyme immunoassays; enzyme-linked immunosorbant assays (ELISA) and enzyme-multiplied immunoassay techniques (EMIT). S. C. Anderson & S. Cockayne, *Clinical Chemistry: Concepts and Applications*, W. B. Saunders (1993) Philadelphia, Pa. In enzyme immunoassays, the process is catalytic such that multiple detectable labels are formed, giving the possibility of enhanced sensitivity.

Electrochemiluminescence (ECL) immunoassays are conventionally carried out with antibody conjugated to the label, which is generally a derivative of tris(bipyridyl) ruthenium(II) (abbreviated as $Ru(bpy)_3^{2+}$) G. Blackburn et al. (1991) Clin. Chem. 37, 1534–1539. In these assays, every antibody has a limited number of $Ru(bpy)_3^{2+}$ molecules on its surface (for example, 6–8).

Compositions and methods have now been discovered for the preparation and uses of β-lactamase-conjugated antibodies in ECL-based immunoassays. For example, the enzyme β-lactamase can efficiently hydrolyze $Ru(bpy)_3^{2+}$ substituted penicillins. The penicillins, termed Ru-Amp and Ru-APA, are only very weakly electrochemiluminescent, but when they are hydrolyzed by β-lactamase according to the present invention they become strongly electrochemiluminescent. The presence of β-lactamase therefore can be detected with a high level of sensitivity in an ECL instrument using either of these compounds. As opposed to conventional ECL immunoassays where the $Ru(bpy)_3^{2+}$ label is directly attached to the antibody, in the enzyme-based ECL immunoassays of the present invention, the electrochemiluminescently-active ruthenium complex is catalytically generated by the enzyme attached to the antibody surface. Thus, instead of one antibody permitting a few (typically 6–8) ruthenium labels to generate light, one antibody-enzyme complex can generate typically 2000 ruthenium labels per second and could generate as many as 10,000 or more.

SUMMARY OF THE INVENTION

Conventional ECL-based immunoassays employ ruthenium labeled antibodies. In the present invention, an immunoassay has been discovered in which the ruthenium-labeled antibody is replaced with an enzyme-labeled antibody. The enzyme is β-lactamase. Tripropylamine (TPA) or similar reductants are omitted from the solution and, for example in the case of infection related assays, ruthenium-labeled penicillins are used instead. In the presence of β-lactamase-labeled antibody, the ruthenium labeled substrates are catalytically hydrolyzed, generating an enormous increase in ECL. The assay is superior to the use of ruthenium-labeled antibody immunoassays because enzyme-generated ECL-active ruthenium is a catalytic process, forming many ECL active molecules.

Broadly stated, the invention contemplates an electrochemiluminescence based immunoassay for the detection of analytes. The invention employs enzymes such as β-lactamases, proteases or oxido-reductases conjugated to antibodies and ECL labels and enzyme substrates, preferably ECL label substituted substrates such as ECL label substituted antibiotics, peptides, and nicotinamide adenine dinucleotide (NADH) which together provide an antibody-enzyme complex which can catalytically generate up to thousands of ECL active labels per second.

Central to use of electrochemiluminesence methodology as a measuring system for analytes was the recognition that β-lactamase can efficiently hydrolyze $Ru(bpy)_3^{2+}$ substituted penicillins. The penicillins, Ru-Amp and Ru-APA, are only very weakly electrochemiluminescent but when they are hydrolyzed by β-lactamase they become strongly electrochemiluminescent.

Various assay formats can be employed in the practice of the invention as will be apparent to those skilled in the art. These include a sandwich assay using, for example, magnetic beads or other solid support such as carbon fibrils, a competitive assay using antigen conjugated to free β-lactamase, a competitive assay where the β-lactamase is a recombinant protein containing a segment that is bound by an antibody that also binds the chosen analyte wherein the enzyme is inactivated by antibody binding, and ELISA where β-lactamase is a reporter on a secondary antibody. *The Immunoassay Handbook*, D. Wild, Ed. (1994) Stockton Press, New York.

DETAILED DESCRIPTION OF THE INVENTION

Figure 1:
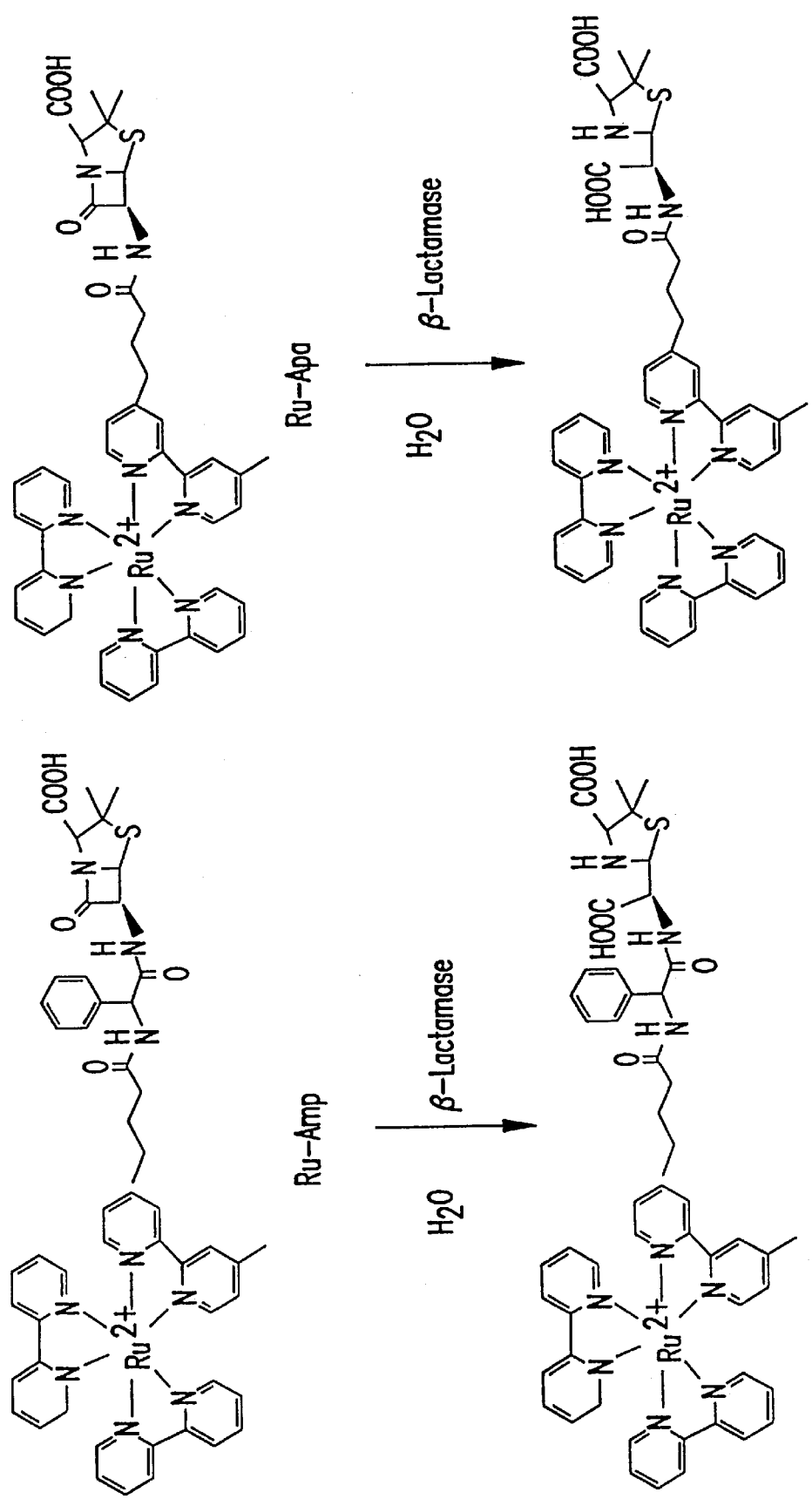
FIG. 1 shows hydrolysis of Ru-AMP and Ru-APA by β-lactamase.

The preferred method of measuring analyte using the electrochemiluminescence based immunoassay is by the following sequential steps:

1. In an analyte-containing solution, admix a magnetic bead-immobilized anti-analyte antibody with a β-lactamase anti-analyte antibody conjugate.
2. After allowing antibodies to bind to analyte to create an antibody-analyte-antibody "sandwich", immobilize the beads with a magnet, wash extensively to remove non-analyte interfering molecules and unbound β-lactamase anti-analyte antibody conjugate.
3. Add ECL-labeled substrate to beads, allow the enzyme to react, the optimum reaction time being determined by the expected concentration of the analyte, and withdraw the supernatant, with no beads.
4. Measure the electrochemiluminescence of the supernatant and compare it to a standard curve of hydrolyzed ECL-labeled substrate concentration vs. electrochemiluminescence. The measurement can be carried out on an ORIGEN® Analyzer by following the instructions in the Operators Manual therefor, available from IGEN, Inc., 16020 Industrial Drive, Gaithersburg, Md. 20877 U.S.A.

According to the invention, an ECL detectant such as $Ru(bpy)_3^{2+}$ is substituted on a substrate such as an antibiotic, peptide or NADH. An enzyme labeled anti-analyte also is prepared using β-lactamase. When the ECL substituted substrate is placed in the presence of the β-lactamase-labeled antibody, the substrate is catalytically hydrolyzed forming the excited state of the detectant, $Ru(bpy)_3^{2+*}$, in substantial quantities. The excited state decays to the ground state through a normal fluorescence mechanism, emitting a photon having a wavelength of 620 nm.

Organic compounds which are ECL detectants include, for example, rubrene and 9,10-diphenyl anthracene. Many organometallic compounds also are ECL detectants, and the most preferable are Ru-containing compounds, such as ruthenium II tris-bipyridine chelate, and Os-containing compounds. Detectants useful in the presently disclosed invention are described in U.S. Pat. No. 5,310,687, the contents of which are incorporated herein by reference.

These detectants are stable for long periods. In addition, the detectants are safe and relatively inexpensive. They give a highly characteristic signal and do not occur in nature. Measurements based on luminescence of such detectants are sensitive, fast, reproducible and utilize simple instrumentation. The signal is generated repeatedly by each molecule of the detectant, thereby enhancing the sensitivity with which they may be detected. The preferred electrochemiluminescent detectants of the present invention are conveniently referred to herein as $Ru(bpy)_3^{2+}$. Various amounts of this detectant, or its equivalent, may be employed. These detectants also have the advantage that they can be used directly in a biological sample without pretreatment of the sample.

The energy necessary for formation of the excited state arises from the hydrolysis of β-lactam or peptide or by reduction of $NAD^+$ to NADH. The excited-state $Ru(bpy)_3^{2+*}$ decays through a normal fluorescence mechanism, emitting a photon at 620 nm.

Quantification of the $Ru(bpy)_3^{2+}$ detectant can be readily automated with relatively uncomplicated instrumentation. The heart of the instrument is the electrochemical flow cell, containing the working electrodes and counter electrodes for initiation of the ECL reaction. Both of the electrodes are preferably fabricated from gold, but other materials have been used with various degrees of success. A potentiostat is used to apply various voltage waveforms to the electrodes, and a single photomultiplier tube (PMT) is used to detect the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the detectant is quantified by applying a ramp voltage to the electrodes and measuring the emitted light. After the measurement, a high pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. Measurements of the working electrode current and the ECL intensity can be induced, for example, by the application of a triangle wave to the electrodes. The applied voltage as shown is actually the voltage measured at the Ag/AgCl reference electrode and includes the effects of a significant uncompensated resistance. Consequently, the actual voltage applied at the working electrode is substantially less than that depicted. The triangle waveform rises from 565 to 2800 millivolts (mV) at a rate of 750 millivolts per second (mV/s) and then decreases at the same rate to 1000 mV. Oxidation of both the β-lactam substrate and $Ru(bpy)_3^{2+}$ becomes evident when the applied voltage reaches 1100 mV and produces a luminescence. The intensity of the luminescence increases with the applied voltage until the substrate at the surface of the electrode is depleted, resulting in decreased intensity. The intensity of the observed luminescence is great enough that it can easily be measured with conventional photomultipliers operating either in photon-counting or current modes.

The preferred method of measuring analyte using the electrochemiluminescence based immunoassay is by the following sequential steps:

1. In an analyte-containing solution, admix a magnetic bead-immobilized anti-analyte antibody with a β-lactamase anti-analyte antibody conjugate.
2. After allowing antibodies to bind to analyte to create an antibody-analyte-antibody "sandwich", immobilize the beads with a magnet, wash extensively to remove non-analyte interfering molecules and unbound β-lactamase anti-analyte antibody conjugate.

3. Add ECL-labeled substrate to beads, allow the enzyme to react, the optimum reaction time being determined by the expected concentration of the analyte, and withdraw the supernatant, with no beads.

4. Measure the electrochemiluminescence of the supernatant and compare it to a standard curve of hydrolyzed ECL-labeled substrate concentration vs. electrochemiluminescence. The measurement can be carried out using established procedures on the ORIGEN® Analyzer.

The sample to which the β-lactam of interest has been added is then placed in a measuring cell to obtain an initial reading. Typically the β-lactam of interest is added in concentrations between 10 micromolar and 1.0 millimolar. The electrochemiluminescent detectant is typically present at $10^{-6}$M concentrations (range 1–15 µM). The sample containing cell is then incubated for a sufficient period of time to insure that β-lactamase catalyzed hydrolysis can occur if the enzyme is present. This period of time typically varies between 5 minutes and 2 hours. Longer and shorter periods of time are possible depending on sample and reagent concentrations. Since all that is involved is empirical parameters, their values can be determined using conventional techniques.

After incubation occurs, a second reading is taken. The difference in readings, if any, correlates with β-lactamase activity present in the sample. See FIG. 2 in this regard.

Accordingly, the apparatus and methodology suitable for the performance of the process of this invention include, as noted earlier, those shown in U.S. Pat. Nos. 5,068,088, 5,061,455, 5,093,268, and 5,147,806 and 5,221,605 which patents are expressly incorporated herein by reference. In addition, electrochemiluminesence molecules for use in the measuring system as detectants include those bidentate aromatic heterocyclic nitrogen-containing ligands of ruthenium and osmium described in U.S. Pat. No. 5,310,687, which patent has been expressly incorporated herein by reference.

Reagent kits containing the materials necessary for the performance of the assays can be assembled to facilitate handling, and foster standardization. Materials to be included in the kit may vary depending on the ultimate purpose. Typically the kit would include the electrochemiluminescent detectant, necessary buffers, and standards. The standards can be chemical reagents or data (empirical) in printed or electronic form necessary for the calibration needed for performance of the assay.

EXAMPLES

Notwithstanding the previous detailed description of the present invention, applicants provide below specific examples solely for purposes of illustration and as an aid to understanding the invention. The examples are both non-limiting and nonexclusive. Accordingly, the scope of applicants' invention as set forth in the appended claims is to be determined in light of the teachings of the entire specification.

Example 1
Preparation of $Ru(bpy)_3^{+2}$-labeled β-lactam Antibiotics
(a) Preparation of $Ru(bpy)_3^{+2}$-labeled 6-aminopenicillanic Acid ("Ru-APA")

Figure 3:
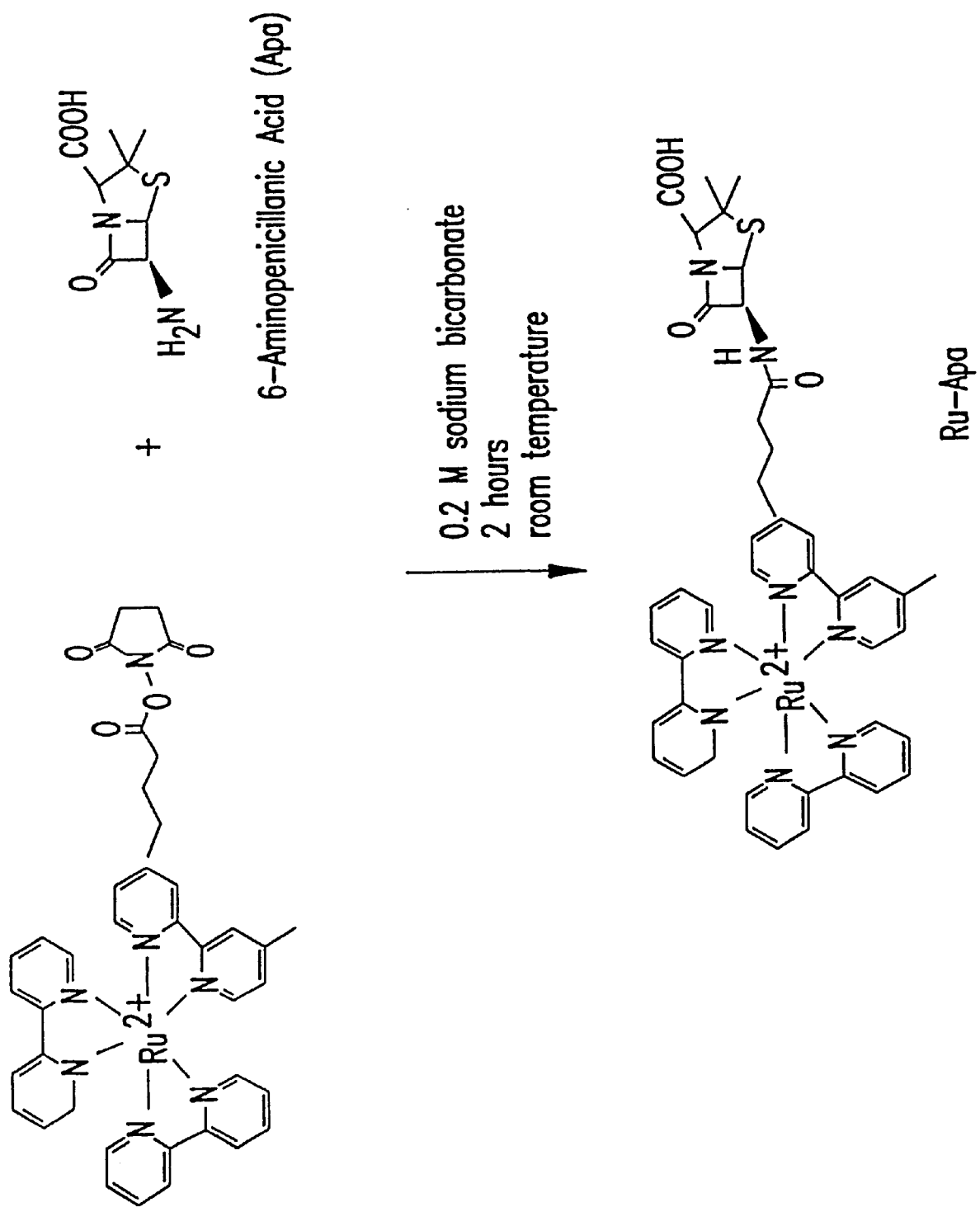
FIG. 3 shows the synthesis of Ru-APA.

$Ru(bpy)_3^{+2}$-NHS ester (15 mg) (IGEN, Inc., Rockville, Md., USA) in acetonitrile (250 µL) was mixed with 6-aminopenicillanic acid (12.4 mg) in 0.2 M sodium bicarbonate, pH 8.0 (350 µL) and the reaction was allowed to proceed at room temperature for 2 hours (FIG. 3). Ru-APA was purified with a Waters HPLC system (Milford, Mass., USA) equipped with a PROGEL™-TSK CM-5PW column (7.5 cm×7.5 mm) (Supelco, Inc., Bellefonte, Pa., USA) using a 1.0 mL/minute, 20-minute linear gradient from 20–100 mM sodium phosphate, pH 7.0. Substrate was quantitated spectrophotometrically by measuring the absorbance of the ruthenium complex (the molar extinction coefficient at 453 nm is 13,700 $M^{-1}$ $cm^{-1}$).

(b) Preparation of $Ru(bpy)_3^{+2}$-labeled Ampicillin ("Ru-AMP")

Figure 2:
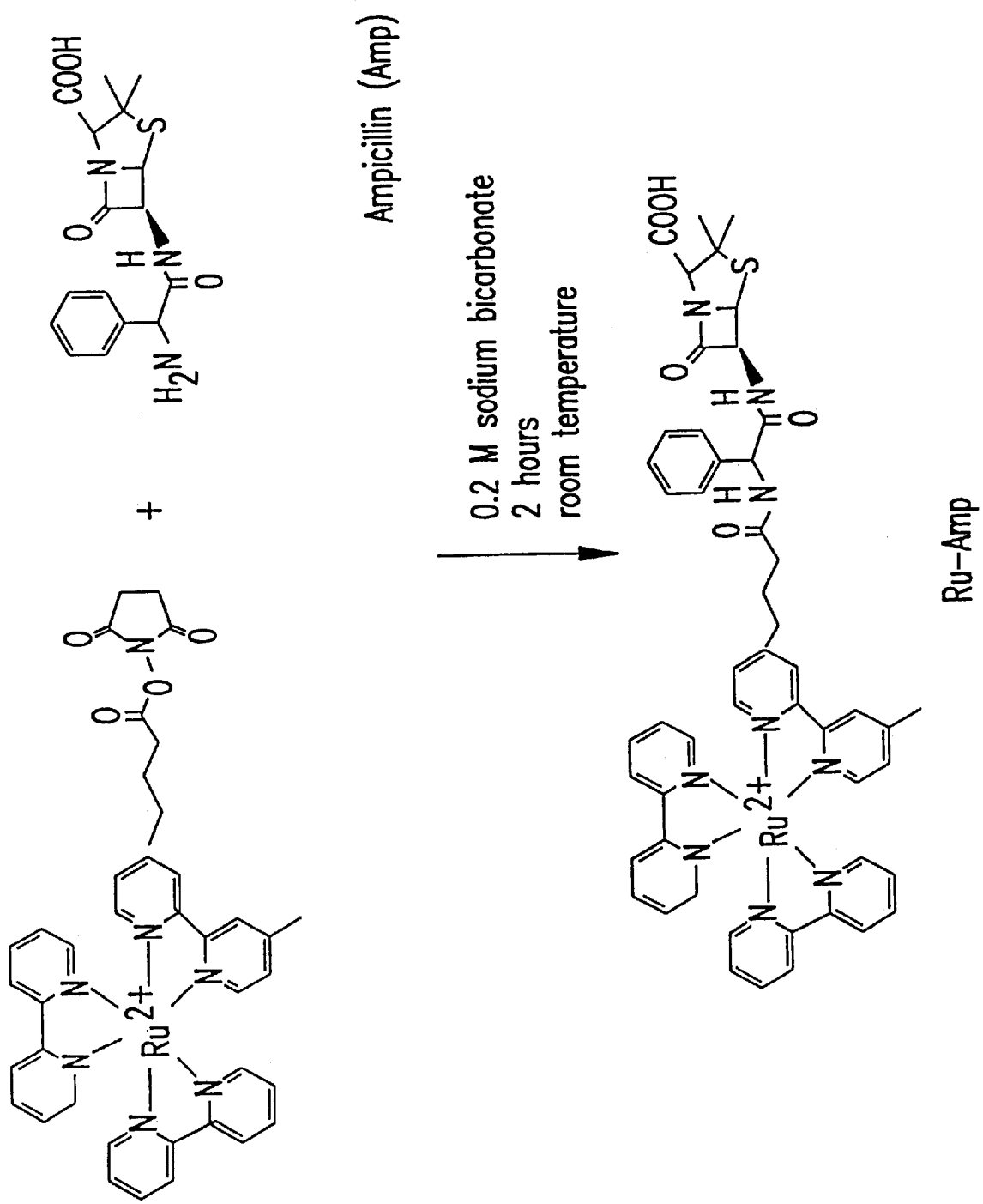
FIG. 2 shows the synthesis of Ru-AMP.
Figure 4:
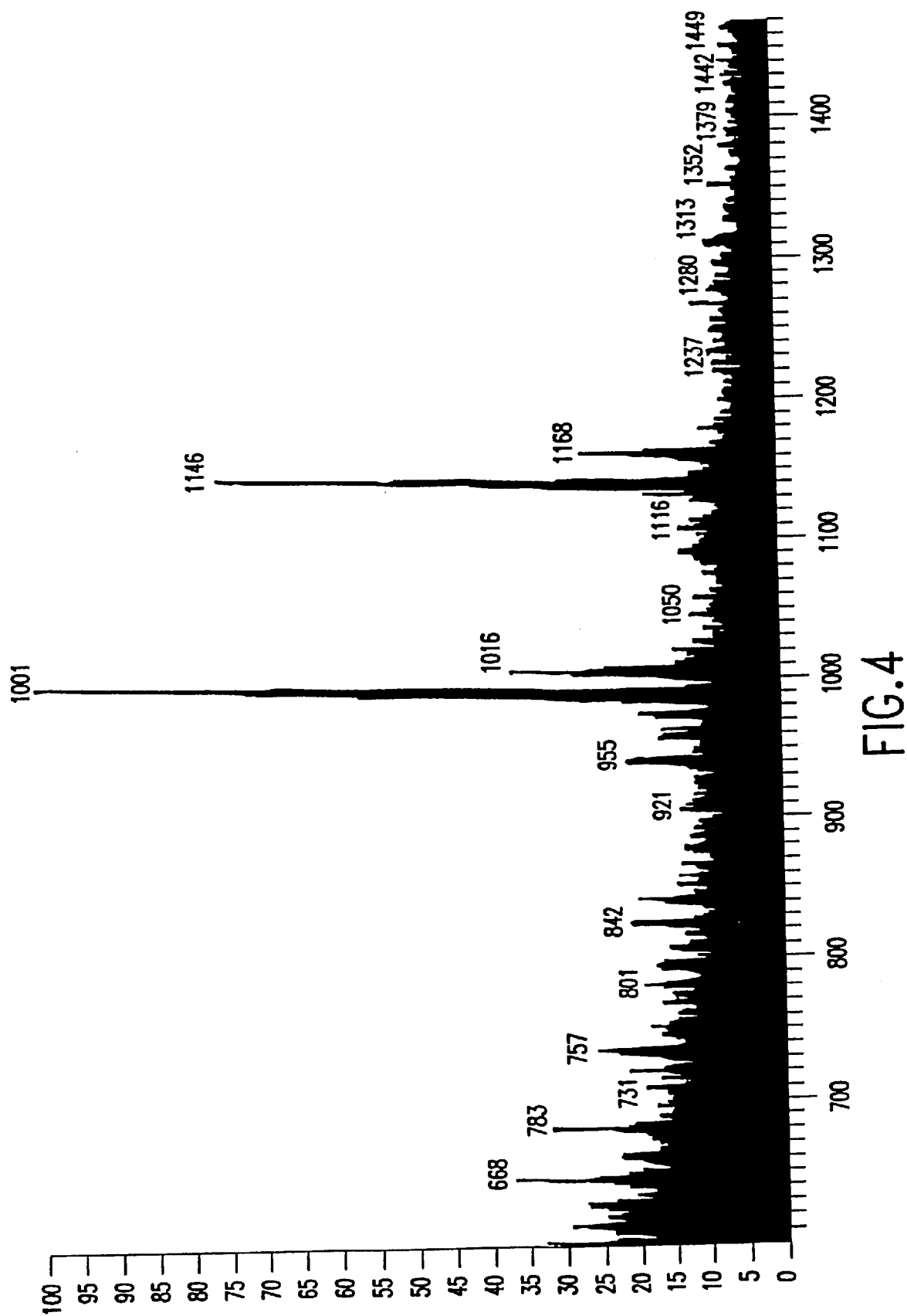
FIG. 4 shows the mass spectrum of the ammonium hexafluorophosphate salt of Ru-APA.
Figure 5:
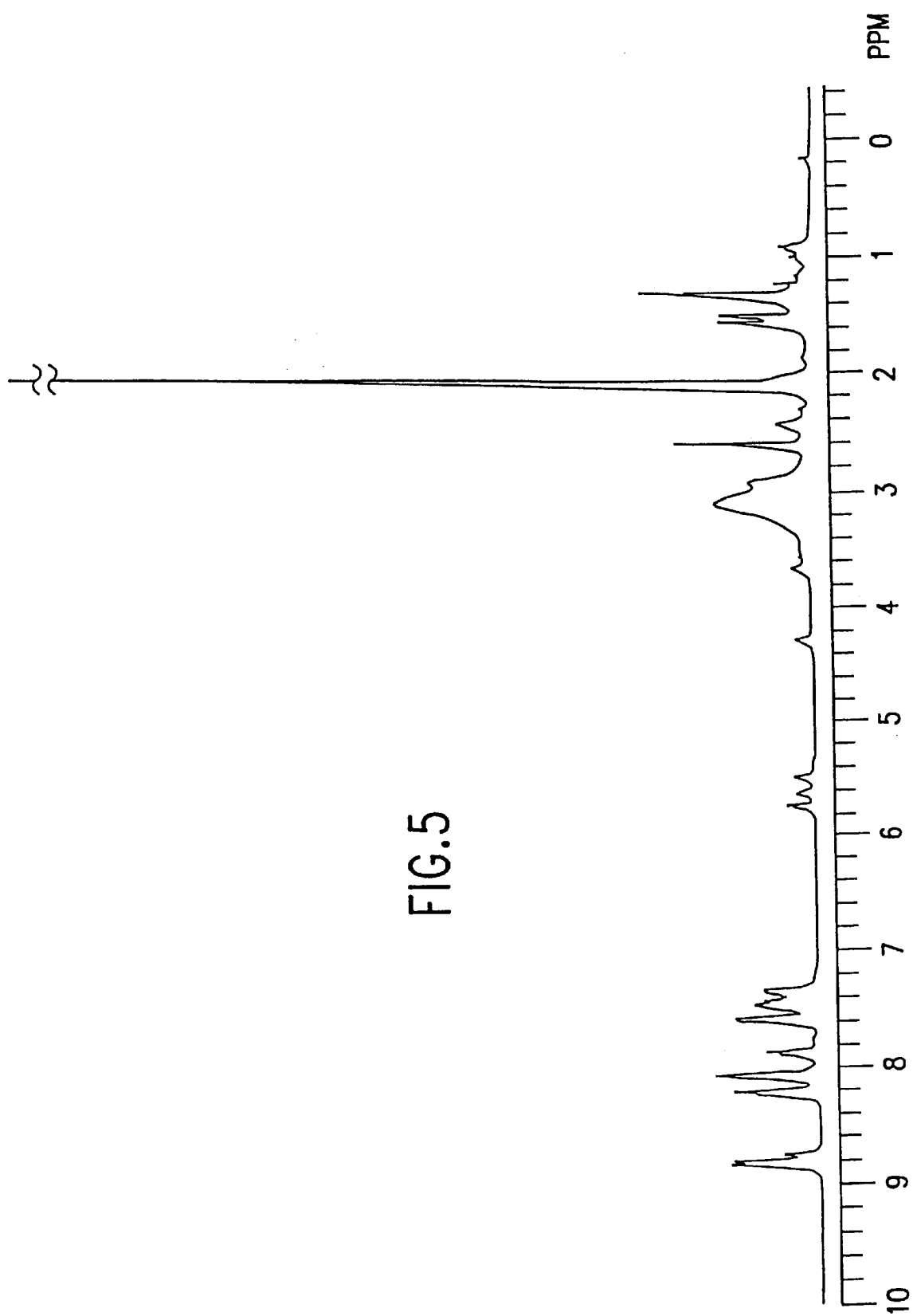
FIG. 5 shows the proton NMR spectrum of the ammonium hexafluorophosphate salt of Ru-APA.

$Ru(bpy)_3^{+2}$-NHS ester (15.1) mg in acetonitrile (250 µL) was mixed with ampicillin (29.1 mg) in 0.2 M sodium bicarbonate, pH 8.0 (250 µL) and the reaction was allowed to proceed at room temperature for 2 hours (FIG. 2). Ru-AMP was purified using a Waters HPLC system (Milford, Mass., USA) equipped with a PROGEL™-TSJ CM-15PW column (7.5 cm×7.5 mm) (Supelco, Inc., Bellefonte, Pa., USA) using a 1.0 mL/minute, 15-minute linear gradient from 20–180 mM sodium phosphate, pH 7.0. Substrate was quantitated spectrophotomerically by measuring the absorbance of the ruthenium complex (the molar extinction coefficient at 453 nm is 13,700 $M^{-1}$ $cm^{-1}$). Following formation of the amnmonium hexafluorophosphate salt, the structure and purity of Ru-AMP was confirmed by mass spectroscopy and proton NMR (FIGS. 4–5).

(c) Preparation of other $Ru(bpy)_3^{+2}$labeled β-lactmans

Figure 6:
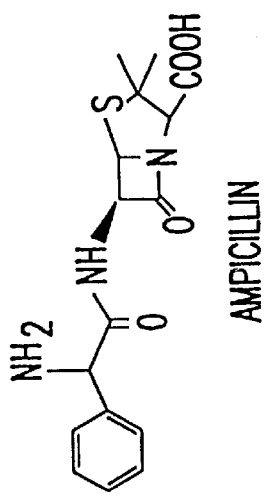
FIG. 6 shows the structures of five specific β-lactams.
Figure 6:
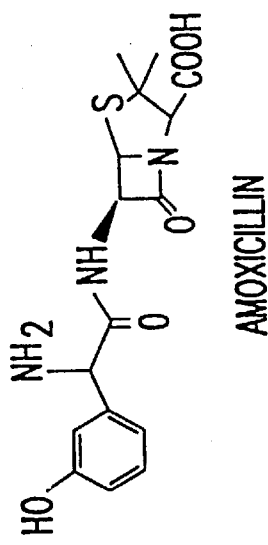
Figure 6:
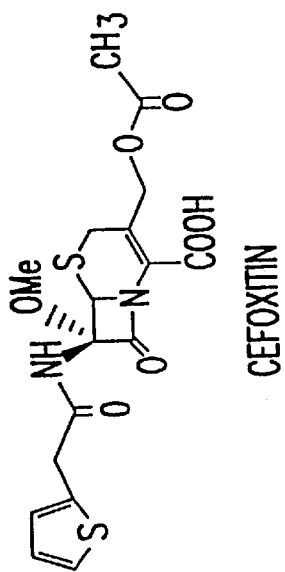
Figure 6:
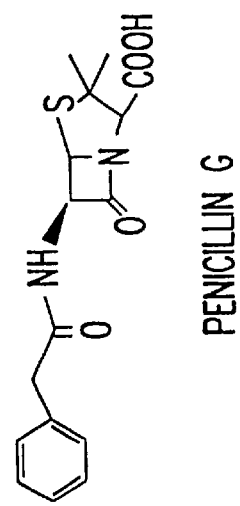
Figure 6:
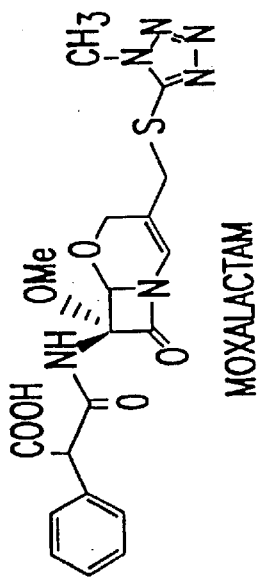

Other β-lactmans, such as 7-aminocephalosporanic acid, that have a primary amine in their structures can also react with $Ru(bpy)_3^{+2}$-NHS ester to form similar conjugates as described above. The reaction and purification conditions will be similar potentially difering somewhat in ways solvable by one skilled in the art. FIG. 6 shows the structure of 5 specific β-lactams.

Example 2
ECL Assay of Ru-AMP Hydrolysis

Figure 7:
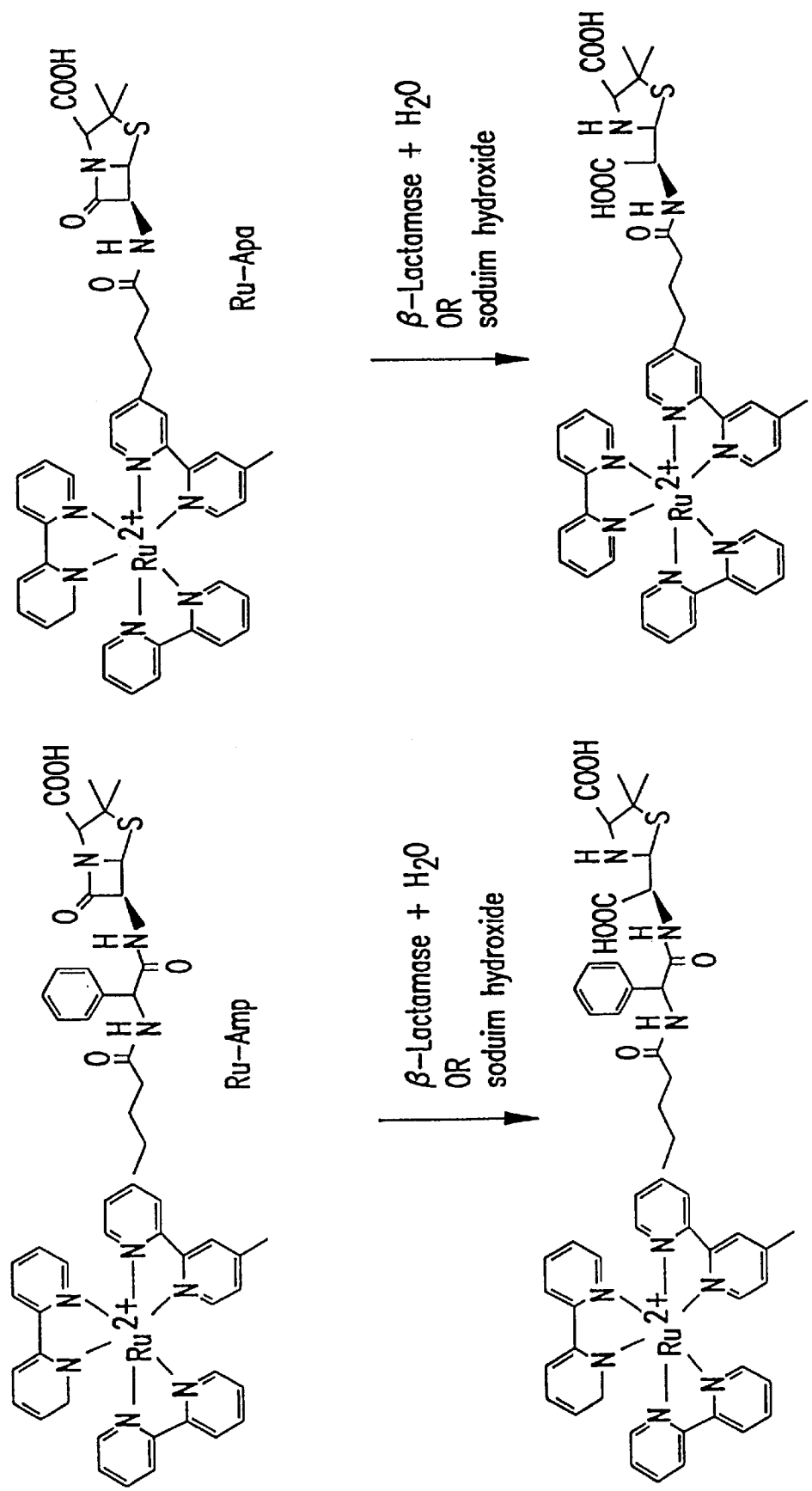
FIG. 7 shows the hydrolysis by NaOH or by β-lactamase enzyme of Ru-AMP (left side) and of Ru-APA (right side).

Experiments were performed to compare the ECL properties of Ru-AMP (conjugated) with $Ru(bpy)_3^{+2}$ and ampicillin mixtures (nonconjugated). ECL properties were compared both before and after NaOH and enzymatic hydrolysis (FIG. 7).

Ru-AMP was found to be a very good substrate of β-lactamase. Hydrolysis of Ru-AMP (33 µM) by β-lactamase I from *Bacillus cereus* (0.3 nM) was monitored spectrophotometrically at 240 nm using a Hitachi U3200 spectrophotometer (Danbury, Conn., USA) at 25.0° C. in 0.1 M sodium phosphate, pH 7.0. Half-time ($t_{1/2}$) analysis gave a $k_{cat}/K_m$ for enzymatic hydrolysis of Ru-AMP of $3.9×10^8$ $min^{-1}M^{-1}$.

Figure 8:
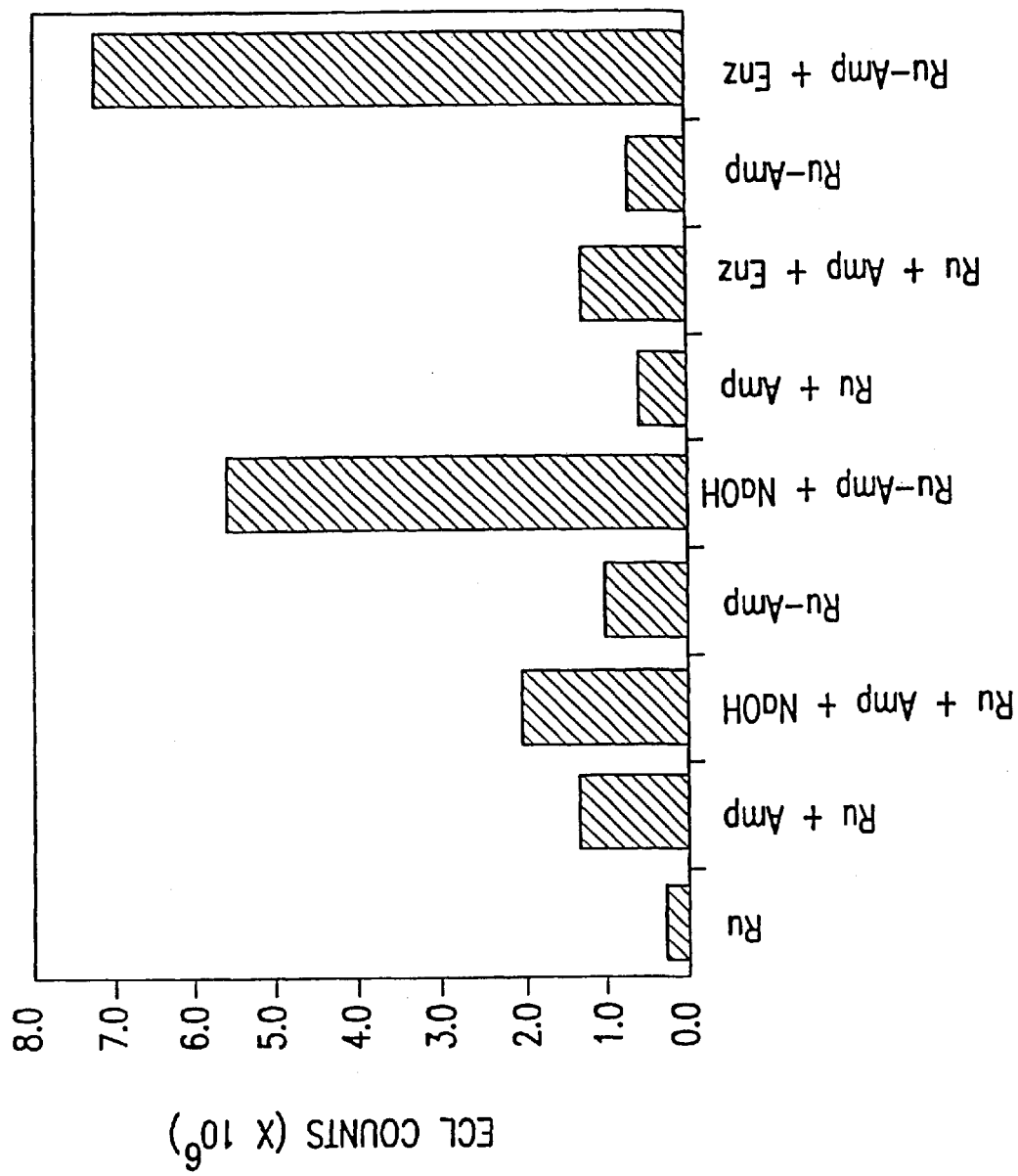
FIG. 8 shows the comparison of measured ECL for a series of different samples.

The ECL properties of equimolar mixtures of $Ru(bpy)_3^{+2}$ and ampicillin (hydrolyzed or unhydrolyzed) were compared to the same concentration of the Ru-AMP conjugate (hydrolyzed or unhydrolyzed). In separate experiments, ampicillin and Ru-AMP were hydrolyzed by either 50 mM NaOH (base hydrolysis) or 347 nM β-lactam I from *Bacillus cereus* (enzyme hydrolysis). For base hydrolysis, 50 µL of 5 M NaOH were added to 1.0 mL solutions of deionized water containing either 30.1 µM Ru-AMP or a mixture of 30 µM ampicillin and 30 µM $Ru(bpy)_3^{+2}$. Following 30 minute incubations, the solutions were neutralized with 50 µL of 5 M HCl. For the unhydrolyzed counterpart experiments, 50 µL of 5 M $H_2O$ were added to solutions of either 30.1 µM Ru-AMP or a mixture containing 30.0 µM ampicillin and 30.0 µM $Ru(bpy)_3^{+2}$. Following 30 minute incubations, 50 µL of 5 M NaCl was added to these solutions. The results shown in FIG. 8 demonstrate: (1) that ampicillin hydrolysis by either NaOH or β-lactamase causes an increase in the ECL of the mixtures; and (2) that the increase in the ECL caused by the hydrolysis is dramatically greater when the light-emitting ruthenium complex is covalently linked to ampicillin. With base hydrolysis, ECL increased 1.5-fold when ampicillin was hydrolyzed in a mixture of ampicillin and Ru(bpy)$_3^{+2}$, while ECL increased 5.2-fold when Ru-AMP was hydrolyzed. Similar results were obtained in enzyme hydrolysis: ECL increased 2.1-fold when ampicillin was hydrolyzed in a mixture of ampicillin and Ru(bpy)$_3^{+2}$, while ECL increased 9.8-fold upon hydrolysis of Ru-AMP. The data establishing these conclusions is found in FIG. 8 which shows the experimentally measured electrochemiluminescence of (from left to right):

Ru(bpy)$_3^{+2}$ alone;
Ru(bpy)$_3^{+2}$ plus unhydrolyzed ampicillin;
Ru(bpy)$_3^{+2}$ plus NaOH-hydrolyzed ampicillin;
unhydrolyzed Ru-AMP;
NaOH-hydrolyzed Ru-AMP;
Ru(bpy)$_3^{+2}$ plus unhydrolyzed ampicillin;
Ru(bpy)$_3^{+2}$ plus β-lactamase-hydrolyzed ampicillin;
unhydrolyzed Ru-AMP; and
β-lactamase-hydrolyzed Ru-AMP.

Figure 9:
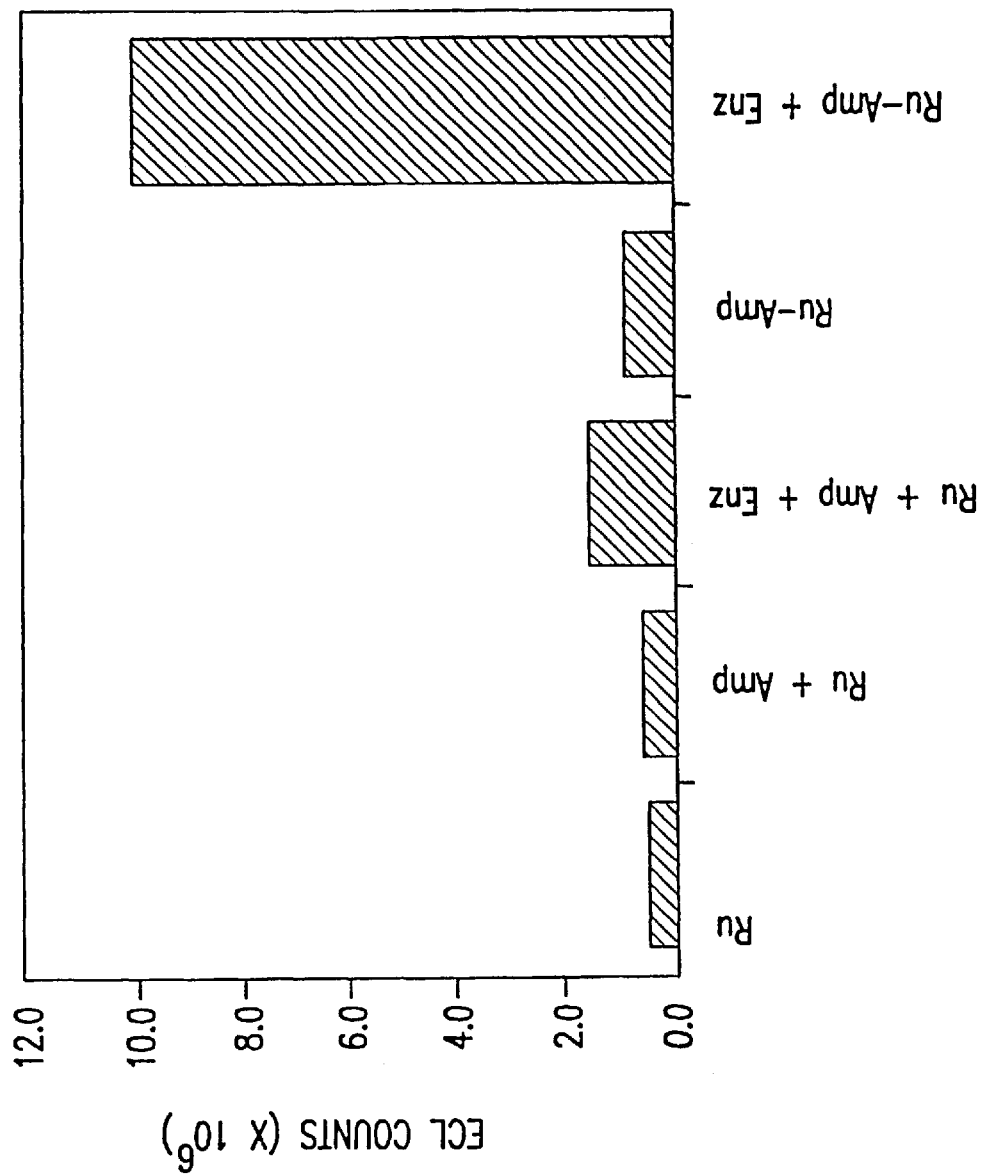
FIG. 9 shows the comparison of measured ECL for a series of different samples.

This work was confirmed in a second experiment using enzyme hydrolysis which differed in that the incubating time with enzyme was lengthened from 30 to 60 minutes (FIG. 9). Here, enzyme hydrolysis caused a 2.5-fold increase in ECL when ampicillin and Ru(bpy)$_3^{+2}$ were conjugated and an 11.1-fold increase in ECL when the Ru-AMP conjugate was hydrolyzed. The data establishing these conclusions is found in FIG. 9 which shows the experimentally measured luminescence of (from left to right):

Ru(bpy)$_3^{+2}$ alone;
Ru(bpy)$_3^{+2}$ plus unhydrolyzed ampicillin;
Ru(bpy)$_3^{+2}$ plus β-lactamase-hydrolyzed ampicillin; unhydrolyzed Ru-AMP; and
β-lactamase-hydrolyzed Ru-AMP.

These results show that Ru(bpy)$_3^{+2}$-conjugation caused intramolecular effects that dramatically increase the experimentally measured luminescence when the β-lactam ring is hydrolyzed.

Figure 10:
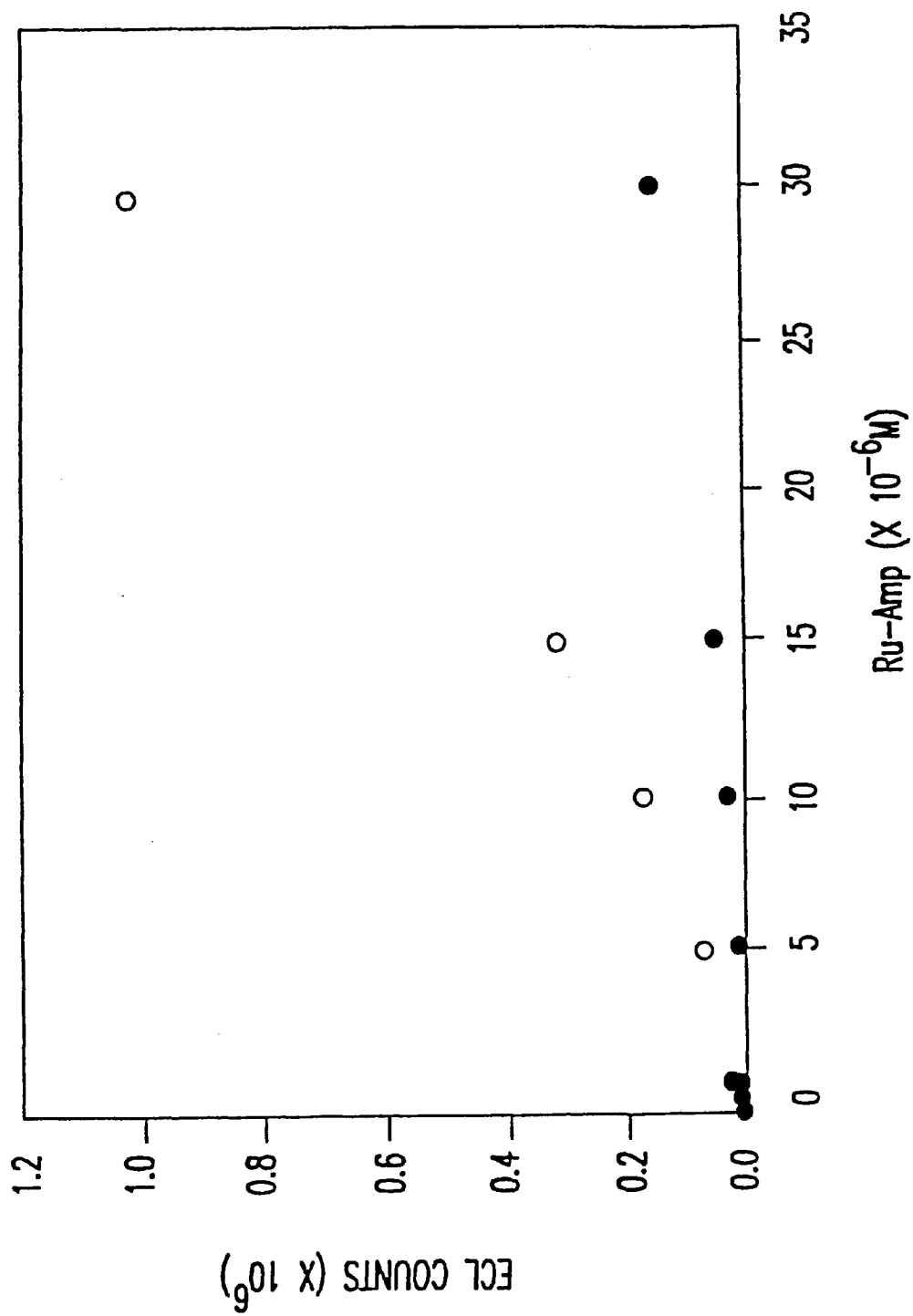
FIG. 10 shows the effect of unhydrolyzed (closed circles) and hydrolyzed (open circles) Ru-AMP concentration on the measured ECL.

FIG. 10 shows that low concentrations of Ru-AMP can be detected by hydrolysis. The lower limit of detection was found to be 50 nM (464 relative ECL counts for hydrolyzed Ru-AMP versus an average instrument reading of −152 relative counts for unhydrolyzed Ru-AMP). This compares favorably to the lower limit for detection of (unconjugated) ampicillin hydrolysis which was 5000 nM.

Example 3
ECL Assay of RU-APA Hydrolysis

It was thought that Ru-APA might have different ECL properties (before and after hydrolysis) from those of Ru-AMP. The differences would be a consequence of the structural differences between APA and AMP, especially the difference in distance between the β-lactam ring and the primary amino group used to conjugate Ru(bpy)$_3^{+2}$-NHS ester (FIG. 7). In Ru-AMP, the β-lactam ring is three bond lengths farther from the amino group than in Ru-APA. Specifically, hydrolysis of Ru-APA (or other β-lactam conjugates) may be more or less sensitively detected by ECL than Ru-AMP hydrolysis.

The ECL properties of the Ru-APA conjugate were compared with those of the mixtures of unconjugated Ru(bpy)$_3^{+2}$ and 6-APA. ECL properties were compared before and after NaOH and enzymatic hydrolysis. The data was then compared to the results of similar experiments with Ru-AMP described in Example 2.

Ru-APA was found to be a very good substrate of β-lactamase. Hydrolysis of Ru-APA (23 μM) by β-lactamase I from *Bacillus cereus* (0.6 nM) was monitored spectrophotometrically at 240 nm using a Hitachi U3200 spectrophotometer (Danbury, Conn., USA) at 25.0° C. in 0.1 M sodium phosphate, pH 7.0. Half-time ($t_{1/2}$) analysis gave a $k_{cat}/K_m$ for enzymatic hydrolysis of Ru-APA of $9.8 \times 10^7$ min$^{-1}$M$^{-1}$.

The ECL properties of equimolar mixtures of Ru(bpy)$_3^{+2}$ and ampicillin (hydrolyzed or unhydrolyzed) were compared with the same concentration of the Ru-APA conjugate (hydrolyzed or unhydrolyzed). In separate experiments, 6-APA and Ru-APA were hydrolyzed by either 50 mM NaOH (base hydrolysis) or 3.8 μM β-lactamase I from *Bacillus cereus* (enzyme hydrolysis).

Figure 11:
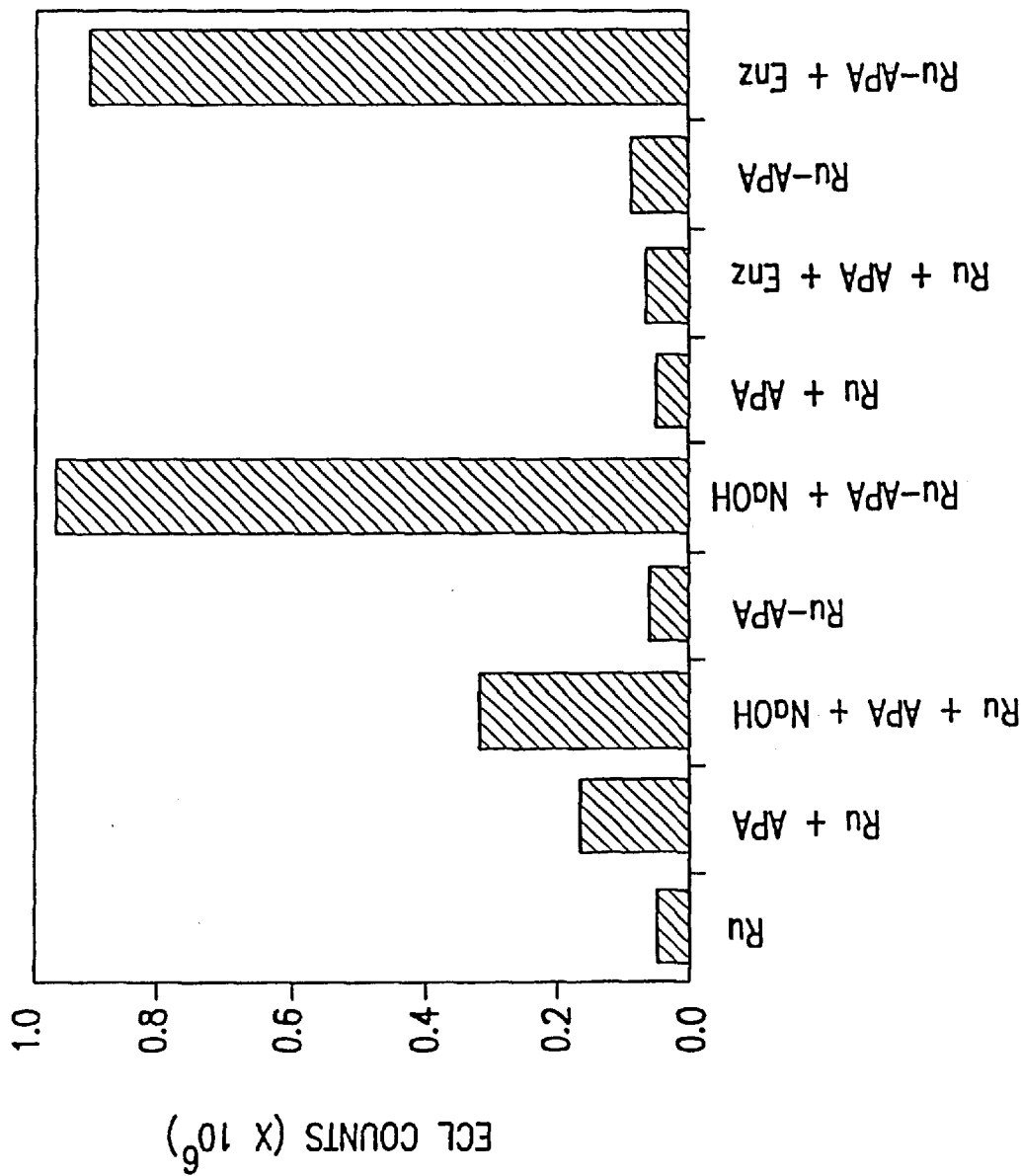
FIG. 11 shows the comparison of measured ECL for a series of different samples.

For base hydrolysis, 50 mL of 5 M NaOH were added to 1.0 mL solutions of deionized water containing either 23.0 μM Ru-APA or a mixture of 23.0 μM APA and 23.0 μM Ru(bpy)$_3^{+2}$. Following 30 minute incubations, the solutions were neutralized with 50 μL of 5 M HCl. For unhydrolyzed counterpart experiments, 50 μL of 5 M H$_2$O were added to solutions of either 23.0 μM Ru-APA or a mixture of 23.0 μM APA and 23.0 μM Ru(bpy)$_3^{+2}$. Following 60 minute incubations, 50 μL of 5 M NaCl was added to these solutions. The results shown in FIG. 11 demonstrate: (1) that 6-APA (conjugated or nonconjugated) hydrolysis by either NaOH or β-lactamase causes an increase in the ECL; and (2) that the increase in the ECL caused by the hydrolysis is dramatically greater when the light-emitting ruthenium complex is covalently coupled to 6-APA. With base hydrolysis, ECL increased 1.9-fold when 6-APA (nonconjugated) in a mixture of 6-APA and Ru(bpy)$_3^{+2}$, was hydrolyzed, while ECL increased 13.2-fold when Ru-APA (conjugated) was hydrolyzed. Similarly with enzyme hydrolysis, ECL increased 1.4-fold when 6-APA (nonconjugated) in a mixture of 6-APA and Ru(bpy)$_3^{+2}$ was hydrolyzed, while ECL increased 31.8-fold when Ru-APA (conjugated) was hydrolyzed. The data establishing these conclusions is found in FIG. 11 which shows the experimentally measured luminescence of (from left to right):

Ru(bpy)$_3^{+2}$ alone;
Ru(bpy)$_3^{+2}$ plus unhydrolyzed 6-APA;
Ru(bpy)$_3^{+2}$ plus NaOH-hydrolyzed 6-APA;
unhydrolyzed Ru-APA;
NaOH-hydrolyzed Ru-APA;
Ru(bpy)$_3^{+2}$ plus unhydrolyzed 6-APA;
Ru(bpy)$_3^{+2}$ plus β-lactamase-hydrolyzed 6-APA;
unhydrolyzed Ru-APA; and
β-lactamase-hydrolyzed APA.

This work clearly demonstrates that conjugation of the 6-APA and the electrochemiluminescent ruthenium complex result in intramolecular effects that increase the electrochemiluminescence when the β-lactam ring is hydrolyzed. Moreover, comparison with the results described in Example 2 for the ampicillin conjugate show that hydrolysis of Ru-APA results in a much greater electrochemiluminescence signal than hydrolysis of Ru-AMP. Because the ruthenium atom is closer to the β-lactam ring in Ru-APA than in Ru-AMP, these results indicate that there may be a critical effect of the distance between the ruthenium complex and the β-lactam ring. Other, as-yet untested β-lactam-Ru(bpy)$_3^{+2}$ conjugates may give an even more dramatic change in the electrochemiluminescence upon β-lactam hydrolysis.

Figure 12:
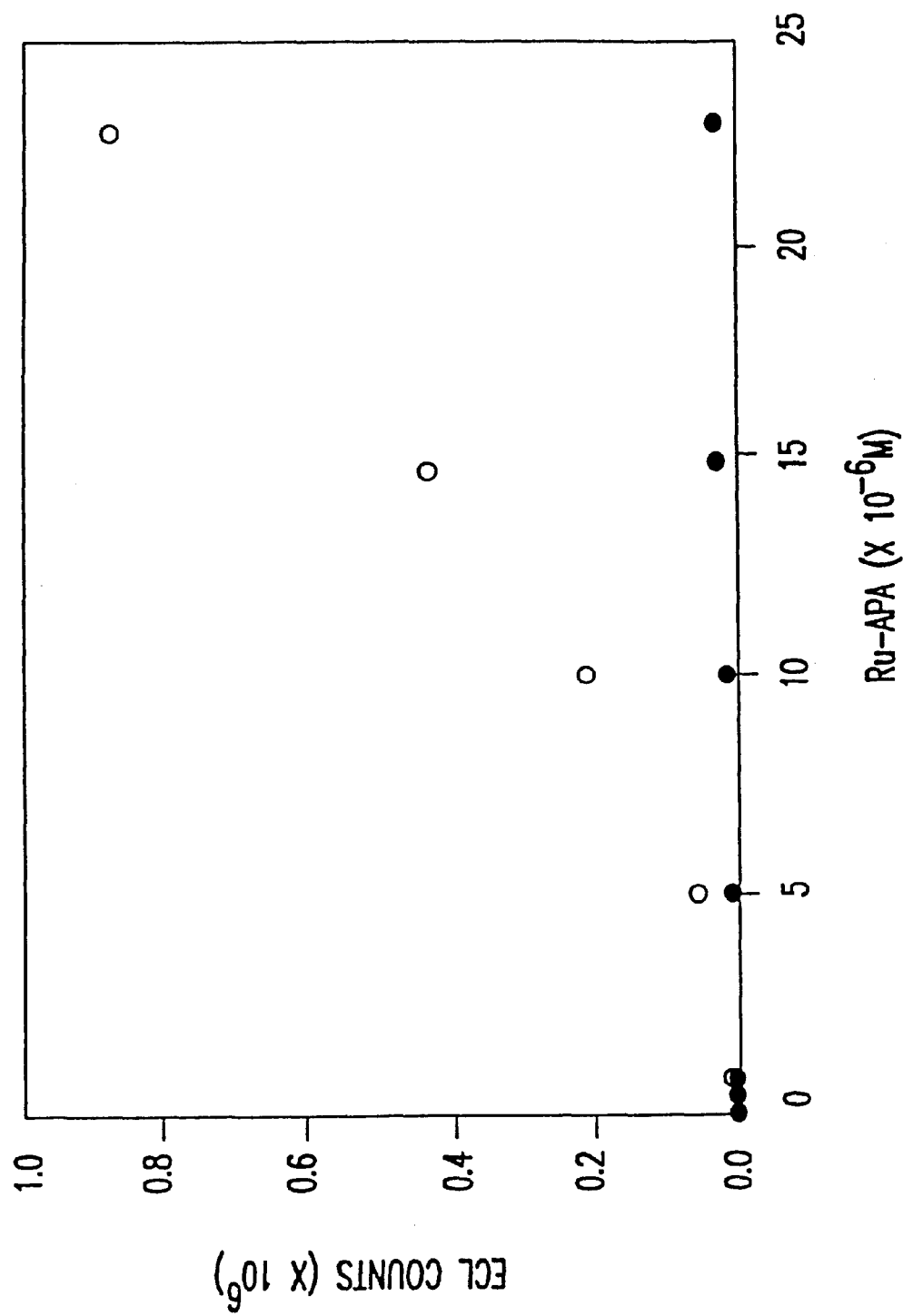
FIG. 12 shows the effect of unhydrolyzed (closed circles) and hydrolyzed (open circles) Ru-APA concentration on the measured ECL.

FIG. 12 shows that the hydrolysis of very low concentrations of Ru-APA can be detected by ECL. More specifically, FIG. 12 shows the effect of unhydrolyzed (closed circles) and hydrolyzed (open circles) Ru-APA concentration on the experimentally measured electrochemiluminescence. The lower limit of detection was found to be 50 nM (an instrument reading of −33 relative ECL counts for hydrolyzed Ru-APA versus an average of −648 relative ECL counts for unhydrolyzed Ru-APA (conjugated)). This compares favorably to the lower limit for detection of (unconjugated) ampicillin hydrolysis which was 50 $\mu$M (in the presence of 10 $\mu$M Ru(bpy)$_3^{+2}$).

Figure 13:
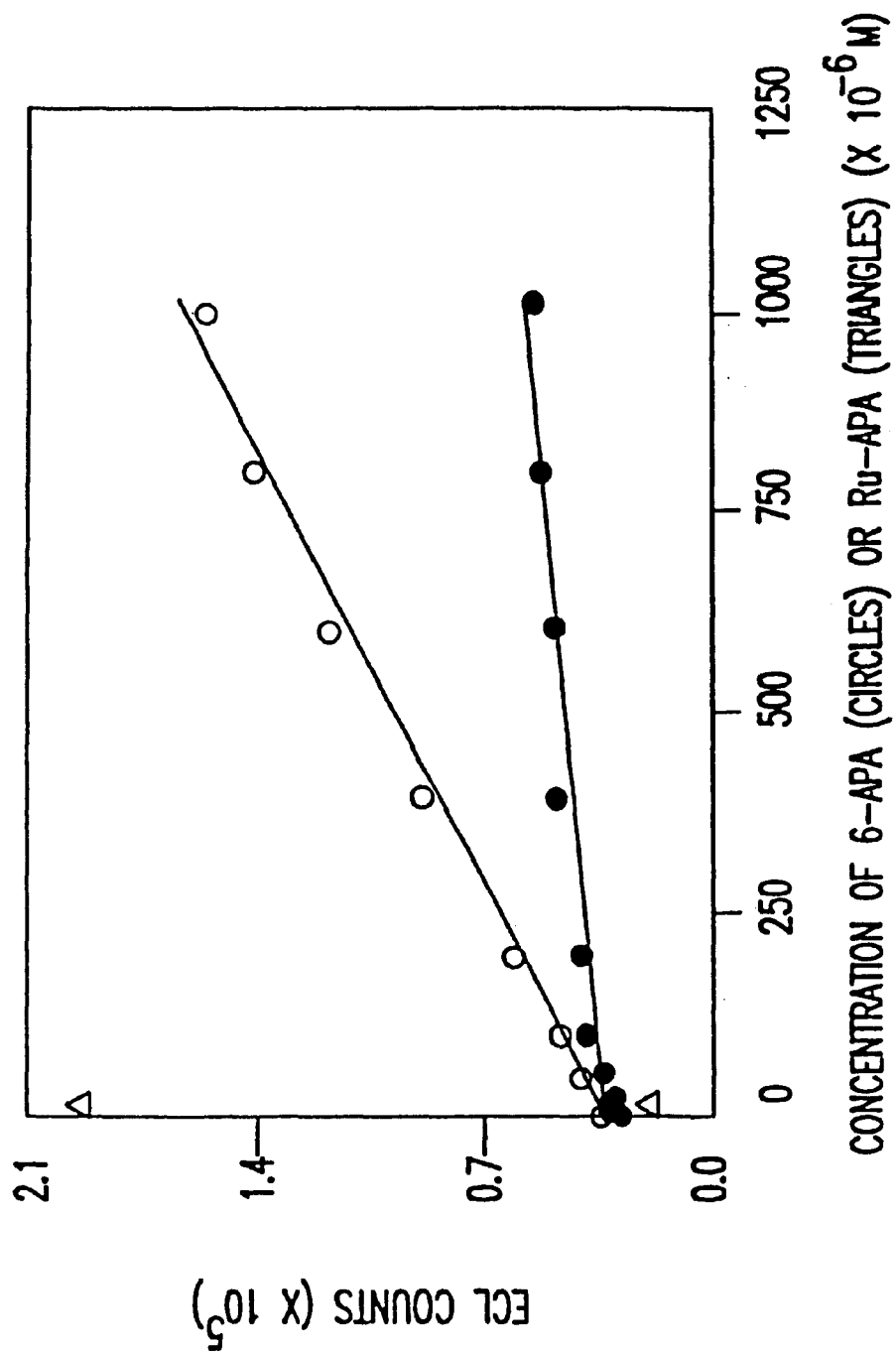
FIG. 13 shows the comparison of measured ECL for a series of different samples.

An experiment was performed to quantitate the advantage of conjugating a $\beta$-lactam to the ECL label, Ru(bpy)$_3^{+2}$. The increase in ECL upon hydrolysis of 10 $\mu$M Ru-APA was compared to an ECL standard curve in which various concentrations of 6-APA (nonconjugated) were hydrolyzed in the presence of 10 $\mu$M Ru(bpy)$_3^{+2}$. By extrapolation of the 6-APA standard curve, the results (FIG. 13) demonstrates that the ECL change upon hydrolysis of 10 $\mu$M Ru-APA (conjugated) is equivalent to the ECL change in the hydrolysis of 1250 $\mu$M 6-APA (nonconjugated) in the presence of 10 $\mu$M Ru(bpy)$_3^{+2}$. This demonstrates that conjugation of Ru(bpy)$_3^{+2}$ and 6-APA results in a 125-fold increase in the ECL change seen during 6-APA hydrolysis. The data establishing these conclusions is found at FIG. 13 which shows a comparison of electrochemiluminescence effects of Ru-APA (conjugated) to Ru(bpy)$_3^{+2}$ plus 6-APA (unconjugated). Triangles represent the electrochemiluminescence of 10 $\mu$M unhydrolyzed (open triangles) and hydrolyzed (closed triangles) Ru-APA. Circles represent the electrochemiluminescence effects of unhydrolyzed (closed circles) and hydrolyzed (open circles) 6-APA (0–1000 $\mu$M) in the presence of 10 $\mu$M Ru(bpy)$_3^{+2}$. Extrapolation in FIG. 13 indicates that the electrochemiluminescence change upon hydrolysis of 10 $\mu$M Ru-APA is equivalent to the electrochemiluminescence change upon hydrolysis of 1250 $\mu$M free 6-APA in the presence of 10 $\mu$M Ru(bpy)$_3^{+2}$.

Example 4

Preparation of an Antibody-$\beta$-Lactamase Conjugate

Antibody-B-Lactamase conjugates have been previously prepared (Yolken et al., J. Immunol. Meth. 73 (1984) 109–123; Svensson et al., Bioconj. Chem. 5 (1994) 262–267). Conjugates are generally prepared using commercially available bifunctional crosslinking agents such as Sulfo-SMCC (sulfosuccinimidyl 4-[N-maleimidomethyl] cyclohexane-1-carboxylate), which was used here. Other methods of covalently linking two proteins have been established and could also be used. Any method is satisfactory as long as the antibody and the enzyme remain biologically active after conjugation.

$\beta$-Lactamase (3.7 mg) was dissolved in 0.500 mL phosphate buffered saline (PBS). Sulfo-SMCC (5 mg) was dissolved in 1.500 mL PBS. The solutions of $\beta$-lactamase and Sulfo-SMCC were mixed and allowed to react for 45 min. at room temperature.

A monoclonal antibody raised against the hapten RT1 (5 mg) was buffer-exchanged into PBS using a Centricon 30 concentrator (Amicon). Dithiothreitol (DTT, 5 mg) was dissolved in PBS, then mixed with the anti-RT1 antibody to give a total volume of 1.300 mL. The mixture is incubated for 30 min. at room temperature to allow DTT to reduce the disulfide bonds of RT1.

The proteins in the two reaction mixtures described above were desalted using SEPHADEX G-25M PD-10 columns (Pharmacia) which had been prequilibrated with PBS. The recovered proteins were quantitated spectrophotometrically at 280 nm. The yields were found to be 1.0 mg $\beta$-lactamase and 3.1 mg antibody. The protein solutions were then mixed giving a 1.5:1.0 molar ratio of $\beta$-lactamase to antibody. The protein solution was rotated at 420° C. for 22 hr. to allow the enzyme-antibody conjugate to form. Following the reaction, the mixture was chromatographed on a Sephacryl S-300 column (Pharmacia). Three major protein peaks were obtained. Because the chromatographic separation was by size, the first peak to elute from the column was expected to be the enyme antibody conjugate.

Example 5

ECL Enzyme Immunoassay

An ECL immunoassay using a $\beta$-lactamase-antibody conjugate can be carried out either with an unconjugated mixture of Ru(bpy)$_3^{+2}$ and a $\beta$-lactam antibiotic (such as APA or Pen G) or, preferably, with a Ru(bpy)$_3^{2+}$-$\beta$-lactam conjugate (such as Ru-APA). Using a conjugated ECL substrate system is preferred because hydrolysis of Ru(bpy)$_3^{2+}$-labelled substrates is much more sensitively detected by ECL than mixtures of the substrate and Ru(bpy)$_3^{2+}$ and the $\beta$-lactamase substrate, Pen G.

Here, an ECL enzyme immunoassay was tested using an antibody-enzyme conjugate (anti-RT1 antibody linked to $\beta$-lactamase as described in Example 4). The presence of the analyte was reported by the $\beta$-lactamase portion of the conjugate, which hydrolyzed the penicillin, Pen G, which is turn caused Ru(bpy)$_3^{2+}$ to emit light by elecrochemiluminescence. The assay was performed in a 96-well plate and ECL was measured by transferring the contents of the wells into test tubes which were read in an ORIGEN® Analyzer.

The analyte (the RT1 hapten conjugated to Bovine Serum Albumin (BSA)) was incubated for 2 hours at 37° C. in a 96-well plate at 0, 0.2, 2.0, and 10.0 $\mu$g/ml to allow it to adhere to the plate. The plate was then washed three times with PBS. To each well was then added 200 $\mu$L of 3% BSA in PBS and the plate was incubated for about 1 hour at 37° C. To each well was added 50 $\mu$L of chromatography fractions from Example 4. The fractions from the first protein peak to elute are suspected to be the antibody-enzyme conjugate while the fractions from the later eluting protein peaks are suspected to be either free antibody or free enzyme, neither of which should give an ECL signal in this experiment. The plate was incubated overnight at 4° C. to allow the antibody-enzyme conjugate to bind to the analyte. The plate was then washed three times with PBS containing 0.05% Tween. To each well was added 75 $\mu$L of 10 mM Pen G and the plate was incubated for 30 min. at room temperature to allow any $\beta$-lactamase present to hydrolyze the Pen G. Following the incubation period, 25 $\mu$L was transferred from each well to test tubes. To each tube was added 25 $\mu$L of 120 $\mu$M Ru(bpy)$_3^{2+}$ and 250 $\mu$L of 0.1 M sodium phosphate, pH 7.0. ECL of the mixtures was then read in an ORIGEN® Analyzer.

Figure 14:
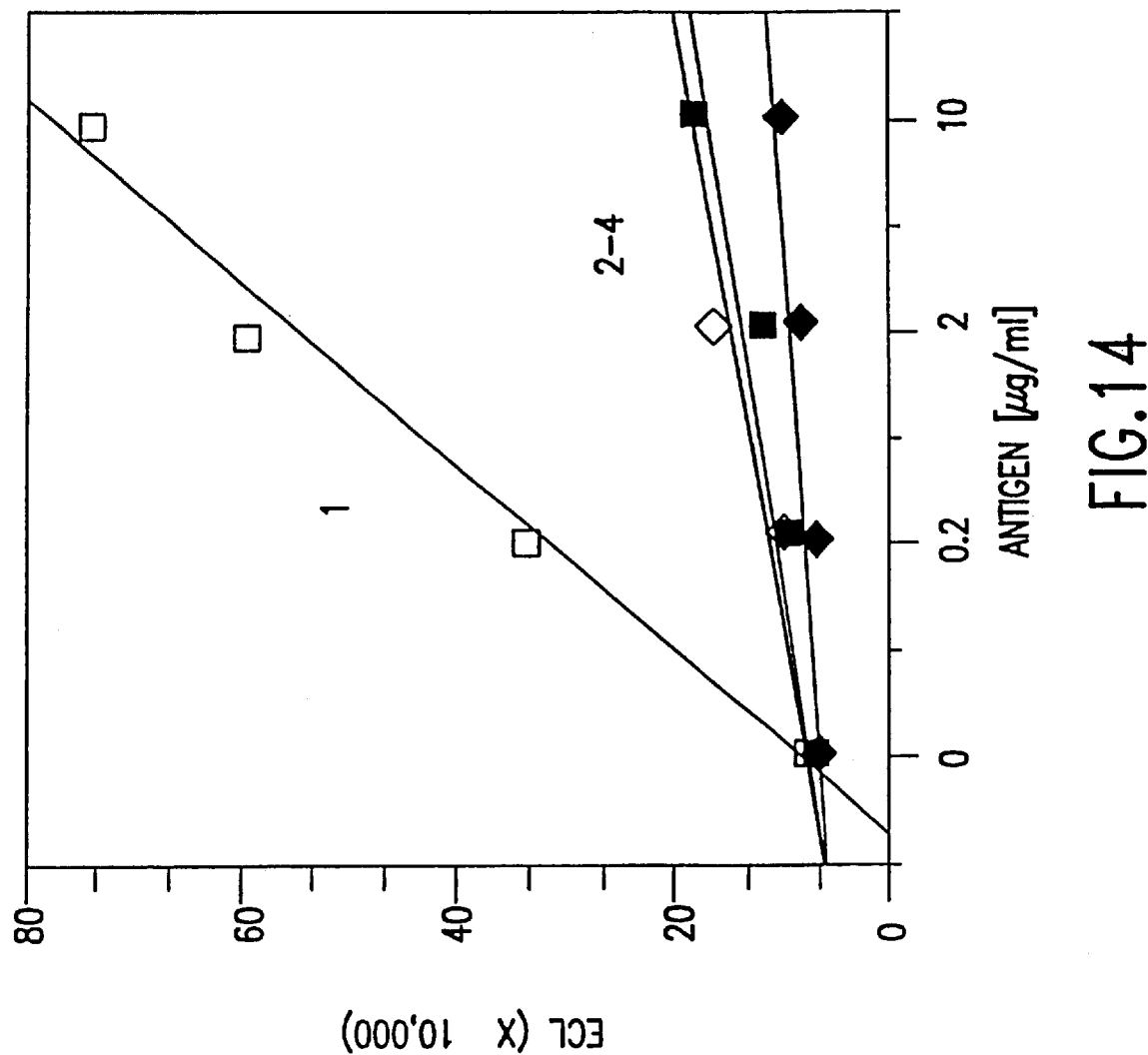
FIG. 14 illustrates an ECL enzyme immunoassay. Various concentrations of an analyte, RT1 hapten, were immobilized in a 96-well plate. To the plate was added either an antibody-enzyme conjugate (anti-RT1 antibody covalently coupled to a β-lactamase enzyme) (Line 1) or non-conjugated antibody or enzyme (Lines 2–4). Following washing to remove protein that did not bind to the analyte, the β-lactamase substrate, Pen G, was added. After incubation to allow any β-lactamase in the plate to hydrolyze the Pen G, the solutions were withdrawn, mixed with $Ru(bpy)_3^{2+}$, and ECL was read in an ECL Analyzer. Line 1 shows the results with the antibody-enzyme conjugate. Lines 2–4 show the results using unconjugated antibody or enzyme.

The results of the ECL enzyme immunoassay are shown in FIG. 14. The protein used in Line 1 was the expected antibody-enzyme conjugate. As can be seen in FIG. 14, the ECL counts in Line 1 increase with increasing analyte concentration. This indicates that the antibody-enzyme conjugate bound to the analyte and hydrolyzed Pen G to a form which promotes Ru(bpy)$_3^{2+}$ ECL. Even the lowest concentration of analyte tested, 0.2 $\mu$g/mL, was detectable. The other lines (2–4) show other chromatographic fractions representing, presumably, free antibody and free enzyme. These lines, which can be considered control experiments, show little increase in ECL with increasing concentrations of analyte. In summary, the antibody-enzyme conjugate was used in an enzyme immunoassay to sensitively detect an analyte using an unconjugated mixture of Pen G and Ru(bpy)$_3^{2+}$. Because the Ru(bpy)$_3^{2+}$-$\beta$ lactam conjugated substrate is much more sensitive in detecting $\beta$-lactam hydrolysis by ECL than a mixture of $Ru(bpy)_3^{2+}$ and β-lactam, the results described here can probably be vastly improved by using a conjugated substrate.

We claim:

1. A method for detecting or quantitating an analyte in a sample said method comprising:
    (a) contacting the sample with
        (i) a binding partner of said analyte or a competitive binder which competes with the analyte in a specific binding interaction, said binding partner or said competitive binder being conjugated to an enzyme;
        (ii) a substrate to said enzyme; and,
        (iii) an electrochemiluminescent detectant, wherein said substrate and the resulting product of said enzyme acting on said substrate differ in their ability to generate electrochemiluminescence at an electrode in the presence of said electrochemiluminescent detectant;
    (b) imposing a voltage upon a working electrode in contact with said sample and thereby causing said electrochemiluminescent detectant to emit electrochemiluminescence;
    (c) detecting or measuring the electrochemiluminescence emitted in step (b); and
    (d) comparing said detection or measurement to a standard to determine whether or in what amount said analyte is present in the sample.

2. A method as recited in claim 1 wherein said electrochemiluminescent detectant is conjugated to said substrate.

3. The method according to claim 2, wherein the enzyme is β-lactamase and the electrochemiluminescent detectant is $Ru(bpy)_3+^2$ or an electrochemilunminescent derivative thereof.

4. The method according to claim 1, wherein said substrate and said electrochemiluminescent detectant are not conjugated to one another.

5. The method according to claim 4, wherein the enzyme is β-lactamase and the electrochemiluminescent detectant is $Ru(bpy)_3+^2$ or an electrochemiluminescent derivative thereof.

6. A method for detecting or quantitating an analyte in a sample said method comprising:
    (a) forming a complex comprising
        (i) said analyte or a competitive binder which competes with the analyte in a specific binding interaction, and
        (ii) a binding partner of said analyte, said binding partner or said competitive binder being conjugated to an enzyme;
    (b) contacting the complex with a substrate to said enzyme and an electrochemiluminescent detectant;
    (c) imposing a voltage upon a working electrode in contact with said complex and thereby causing said electrochemiluminescent detectant to emit electrochemiluminescence;
    (d) detecting or measuring the electrochemiluminescence emitted in step (c); and
    (e) comparing said detection or measurement to a standard to determine whether or in what amount said analyte is present in the sample.

7. The method of claim 6 wherein said substrate and said electrochemiluminescent detectant are conjugated to one another.

8. The method of claim 6 wherein said substrate and said electrochemilunminescent label are not conjugated to one another.

9. The method of claim 6, wherein the enzyme is β-lactamase, a protease or an oxido-reductase.

10. The method of claim 6, wherein the substrate is an antibiotic, a peptide, or nicotinamide adenine dinucleotide.

11. The method of claim 6, wherein the electrochemiluminescent detectant is selected from the group consisting of rubrene, 9,10-diphenyl anthracene, ruthenium containing compounds and osmium containing compounds.

12. The method of claim 11, wherein the electrochemiluminescent detectant is ruthenium II tris-bypyridine chelate.

13. The method of claim 7 wherein the electrochemiluminescence generated in the presence of said electrochemiluminescence detectant by the reaction product of the enzyme working on said substrate/detectant conjugate is higher than the electrochemiluminescence generated by the substrat/detectant conjugate.

* * * * *

UNITED STATES PATENT AND TRADEMARK OFFICE
CERTIFICATE OF CORRECTION

PATENT NO.    : 6,524,865 B1
DATED         : February 25, 2003
INVENTOR(S)   : Martin et al.

It is certified that error appears in the above-identified patent and that said Letters Patent is hereby corrected as shown below:

Title Page,
Item [56], References Cited, U.S. PATENT DOCUMENTS, delete
"4,470,459 A  9/1984  Copland"; substitute -- 4,740,459   4/1998   Chen et al. --

Column 2,
Line 9, change "5,235,808" to -- 5,238,808 --
Line 15, insert -- , with tripropylamine (TPA). Salts of Ru(bpy)$_3^{2+}$ -- after "Ru(bpy)$_3^{2+}$"
Line 28, change "1." after "Francois," to -- I. --
Line 56, change "4,470,459" to -- 4,740,459 --

Column 7,
Line 19, change "10-$^{-6}$M" to -- 10$^{-6}$M --

Column 8,
Line 29, change "Ru(bpy)$_3^{2+}$labeled β-lactmans" to -- Ru(bpy)$_3^{2+}$-labeled β-lactams --
Line 30, change "β-lactmans" to -- β-lactams --

Column 9,
Line 50, change "RU-APA" to -- Ru-APA --

Column 11,
Line 61, change "prequilibrated" to -- pre-equilibrated --
Line 66, change "420º C." to -- 4º C. --

Signed and Sealed this

Tenth Day of February, 2004

JON W. DUDAS
*Acting Director of the United States Patent and Trademark Office*